(12) United States Patent
Link et al.

(10) Patent No.: US 10,952,860 B2
(45) Date of Patent: Mar. 23, 2021

(54) DOUBLE MOBILITY PROSTHESIS

(71) Applicant: Waldemar Link GmbH & Co. KG, Hamburg (DE)

(72) Inventors: Helmut Link, Hamburg (DE); Günther Jendro, Kaltenkirchen (DE); Georg Gradl, Baldham (DE)

(73) Assignee: Waldemar Link GmbH & Co. KG, Hamburg (DE)

(*) Notice: Subject to any disclaimer, the term of this patent is extended or adjusted under 35 U.S.C. 154(b) by 0 days.

(21) Appl. No.: 15/541,898

(22) PCT Filed: Dec. 11, 2015

(86) PCT No.: PCT/EP2015/079419
§ 371 (c)(1),
(2) Date: Jul. 6, 2017

(87) PCT Pub. No.: WO2016/110372
PCT Pub. Date: Jul. 14, 2016

(65) Prior Publication Data
US 2018/0008420 A1    Jan. 11, 2018

(30) Foreign Application Priority Data
Jan. 7, 2015   (DE) .................. 20 2015 100 029.4

(51) Int. Cl.
*A61F 2/34* (2006.01)
*A61F 2/46* (2006.01)
(Continued)

(52) U.S. Cl.
CPC .................. *A61F 2/34* (2013.01); *A61F 2/32* (2013.01); *A61F 2/4637* (2013.01);
(Continued)

(58) Field of Classification Search
CPC ........................................................ A61F 2/34
See application file for complete search history.

(56) References Cited

U.S. PATENT DOCUMENTS 4,619,658 A * 10/1986 Pappas .................. A61F 2/32
                                                    623/22.19
4,642,123 A   2/1987 Noiles
(Continued)

FOREIGN PATENT DOCUMENTS

EP   1776934 A1   4/2007
EP   2489333 A1   8/2012
(Continued)

*Primary Examiner* — Bruce E Snow
*Assistant Examiner* — Melissa A Hoban
(74) *Attorney, Agent, or Firm* — Edwin A. Sisson, Attorney at Law, LLC; Jeffrey J. Banyas (57) ABSTRACT

Provided is a joint replacement with a joint socket (10) having a concave joint surface (11), and with a joint insert (20) having a concave joint surface (21) and a convex joint surface (22) which are each delimited by a peripheral edge (23, 24). The convex joint surface (22) of the joint insert (20) is designed, in the assembled state, to form a first partial joint with the concave joint surface (11) of the joint socket (10). Moreover, the concave joint surface (21) of the joint insert (20) is designed, in the assembled state, to form a second partial joint with the convex joint surface (32) of a joint head (30). The joint socket (10) and the joint insert (20) each have a securing means (12, 25, 26) for preventing dislocation of the joint replacement.

5 Claims, 4 Drawing Sheets

(51) Int. Cl.
*A61F 2/32* (2006.01)
*A61F 2/30* (2006.01)
*A61F 2/36* (2006.01)

(52) U.S. Cl.
CPC ....... *A61F 2/3609* (2013.01); *A61F 2002/305* (2013.01); *A61F 2002/30367* (2013.01); *A61F 2002/30426* (2013.01); *A61F 2002/30593* (2013.01); *A61F 2002/30652* (2013.01); *A61F 2002/3208* (2013.01); *A61F 2002/3233* (2013.01); *A61F 2002/3241* (2013.01); *A61F 2002/345* (2013.01)

(56) References Cited

U.S. PATENT DOCUMENTS

| | | | | |
|---|---|---|---|---|
| 4,714,477 | A * | 12/1987 | Fichera | A61F 2/34 623/22.19 |
| 2003/0171817 | A1 * | 9/2003 | Rambert | A61F 2/32 623/22.17 |
| 2014/0128988 | A1 * | 5/2014 | Muratoglu | A61F 2/30 623/23.11 |
| 2014/0303743 | A1 * | 10/2014 | Choudhury | A61F 2/34 623/22.24 |

FOREIGN PATENT DOCUMENTS

| | | |
|---|---|---|
| FR | 2795302 A1 | 12/2000 |
| FR | 2948013 A1 | 1/2011 |
| WO | 0200141 A1 | 1/2002 |
| WO | 2006084426 A2 | 8/2006 |

\* cited by examiner

DOUBLE MOBILITY PROSTHESIS

PRIORITIES AND CROSS REFERENCES

This patent application claims the priority from International Application No. PCT/EP2015/079419 filed on 11 Dec. 2015 and German Patent Application No. 20 2015 100 029.4 filed on 7 Jan. 2015, the teachings of each of which are incorporated herein by reference in their entirety.

FIELD OF THE INVENTION

The present invention relates to a joint replacement with two partial joints as well as to an insertion aid for said joint replacement.

PRIOR ART

Replacing an injured or worn-out natural joint with an artificial joint is a common procedure. Now, in the meantime, there are artificial joint replacements for a multiplicity of natural joints, such as, for example, for the hip joint, the shoulder joint, the elbow joint, the ankle joint, the finger joint or the knee joint. Total joint replacements are composed of at least two components that are fixed to the opposite bones. Total hip endoprosthesis of this kind thus comprise a joint socket to be implanted in the acetabulum of a patient, as well as a joint head on a prosthesis stem to be anchored in the femur.

Generally, artificial joints are not just copies of natural joints in terms of their dimensions and structure. As regards, for instance, artificial hip joints, the joint heads are frequently given a significantly smaller diameter as compared to the natural joint head. The reason for this is reduced abrasion or the use of ceramics as a prosthetic material. If a ceramic is used, smaller heads offer the advantage that their smaller volume reduces the risk of failure due to manufacturing defects. Furthermore, smaller diameter joint heads will cause less abrasion due to less movement in the joint cavity. On the other hand, larger diameter joint heads offer the advantage of greater stability and lower risk of dislocation, while providing the patient with a greater range of motion.

Double-joint prostheses attempt to implement these advantages arising from the larger joint head diameter in a prosthesis with a small joint head. Such hip endprosthesis generally comprise three components that are movable relative to each other. As compared to the aforementioned standard prostheses, there is provided a joint insert between the hip socket and the femoral head, which is movable relative to the hip socket and the femoral head. Consequently, such a hip endoprosthesis basically combines a large diameter joint prosthesis with a small diameter joint prosthesis, which will hereinafter also be designated as first or large partial joint and as second or small partial joint.

The large joint is formed by the concave surface of the hip socket and the convex surface of the joint insert, while the small joint is formed by the concave surface of the joint insert and the convex surface of the femoral head that is usually connected with a prosthesis stem anchored in a femur.

As a consequence of this multi-joint structure, movements are divided between the large joint and the small joint as a function of their extent. That is to say, the small joint primarily performs movements requiring only a small range of motion, such as normal walking. However, the large joint is also deflected, at the latest when the small joint reaches its maximum deflection, and therefore the possible range of motion of the entire hip joint endoprosthesis is utilized.

Thus, such a sequence of movement minimizes the extent to which the large joint moves, while maintaining the advantages of a large range of motion and a lower risk of dislocation. On the other hand, joint movement preferably takes place for the most part between the bearing surfaces of the small joint, and this contributes to low overall wear of the hip endoprosthesis.

However, in order to ensure that hip endprostheses thus constructed hold together, one of the articulated connections is configured as an enarthrodial joint. Such an enarthrodial joint is characterized in that the convex joint surface of the joint head is enclosed, beyond its equator, by the concave joint surface of the joint socket, thus preventing these components from falling apart. However, such an enarthrodial joint should be capable of being assembled intraoperatively since an already assembled joint makes implantation more difficult and might even be damaged during impaction.

In order for a joint head to be inserted into the opposite joint socket such that the convex joint surface contacts the concave joint surface, the head may be configured to be capable of being snap-fitted into the joint insert. This requires, however, the use of a certain amount of force in order so that the joint head and/or the opening of the socket is deformed to such an extent as to allow the head to come to rest in the socket.

Another option of mounting such a joint is proposed by US patent application 2010/0234963 A1, where the opening in the concave surface of the socket is formed such that the femoral head can be guided therethrough only if rotated 90°. Once introduced, the femoral head can be turned back again so that the socket and the head are aligned with each other. However, in a joint system thus configured, the rim of the femoral head, in the assembled state, is inevitably situated below the socket opening. Therefore, such an arrangement is disadvantageous in that it results, for geometric reasons, in a limited range of motion since the implant stem connected with the femoral head abuts against the rim of the socket opening earlier.

However, the teaching of the present document does not address the age-related risk of dislocation. In elderly patients, the risk of dislocation is additionally increased due to the fact that, apart from being exposed to postoperative strain and damage, their tissue is generally weakened from the outset. This applies, in particular, if the implantation of a joint replacement is preceded by a prolonged phase of restricted mobility due to the worn-out joint. Although this situation can be improved prior to surgery by physiotherapeutic measures, it is desirable to have available further treatment options for such patients which can supplement the limited possibilities of physiotherapeutic measures.

SUMMARY OF THE INVENTION

It is therefore an object of the present invention to provide an insert and a joint system which also prevent dislocation in patients whose constitution is impaired. Another object is to enable simple, intraoperative assembly without compromising the functionality of the joint endoprosthesis, while keeping the strain on the joint components to a minimum.

This object is solved by the combination of features defined in the independent claims. The corresponding dependent claims describe preferred embodiments of the present invention.

To solve the object, the present invention provides a joint replacement with a joint socket having a concave joint surface, and with a joint insert having a concave joint surface and a convex joint surface which are each delimited by a peripheral edge. In this regard, the convex joint surface of the joint insert is designed, in the assembled state, to form a first partial joint with the concave joint surface of the joint socket. Moreover, the concave joint surface of the joint insert is designed, in the assembled state, to form a second partial joint with the convex joint surface of a joint head. Furthermore, the joint socket and the joint insert each have at least one securing means for preventing dislocation of the joint replacement.

The securing means of the joint socket and joint insert make it possible to minimize, or even exclude, the risk of dislocation, particularly in patients with weakened tissue. Thus, even those patients may now receive a joint replacement for whom this was previously difficult or even impossible on account of their tissue condition. The freedom of movement thus regained means a substantial improvement in quality of life for these patients.

In a particularly preferred embodiment of the present invention, dislocation of the respective partial joint is prevented in that a region of the concave joint surface of the joint socket and/or joint insert forms the respective joint into an enarthrodial joint.

The securing means of the joint replacement according to the invention are hence configured in such a manner that the partial joints remain in the assembled state, without their freedom of movement being limited, even when no external force is acting thereon.

Cohesion of the joint components is ensured in that the insertion opening of the receiving joint part is smaller than the external dimensions of the joint part to be inserted. In other words, the insertion opening of the concave joint surface is designed to be smaller than the greatest distance between two points on the convex surface of the insert, at least in the event of a ball joint. Consequently, the region preventing dislocation is situated at the peripheral edge of the concave joint surface. Assuming that the joint has a spherical shape, said region thus constitutes that part of the joint surface which goes beyond its equator.

In another preferred embodiment, the opening diameter of the concave joint surface is 1% to 6%, preferably 2% to 5%, most preferably 3.5% to 5% less than the joint diameter.

This makes it possible to effectively prevent or preclude dislocation of the joint implanted in the patient. Particularly the lower values of these ranges allow the mating joint parts to be assembled by pressing the male joint part into the female joint part. It is preferred thereby for at least one of the mating joint parts to be made of a polymer, notably UHMWPE, if possible. This pressing can be performed before implantation of the joint replacement so as to avoid damage to the patient tissue.

In a particularly preferred embodiment, the securing means of at least one of the partial joints has two preferably detachable securing elements which cooperate to prevent dislocation of the partial joint.

Unlike in the case of assembling the joint by pressing it together as described above, the joint can also be assembled during implantation when using the securing elements. In other words, in the joint replacement according to the invention, it is preferred for only one of the partial joints to be configured as an enarthrodial joint that is assembled by pressing the two joint components together. In this embodiment, however, at least the other partial joint, especially if designed as an enarthrodial joint, should allow assembly by means of detachable securing elements. These enable the aforementioned region of the concave joint surface, which forms the joint into an enarthrodial joint, to be connected with the concave joint surface only after insertion of the mating convex joint part.

The fact that at least one of the partial joints is formed with a securing means having detachable securing elements is moreover advantageous in the event of a reversion as it simplifies the removal of the joint component to be replaced.

In a further particularly preferred embodiment, the two securing elements cooperate by means of a preferably detachable threaded, locking and/or snap connection.

The securing means thus configured is easy to assemble and can moreover also be designed to be detachable.

For instance, the securing means can be formed as a threaded connection as this is easy to assemble, besides being easily detachable. To prevent the securing means of this embodiment from being unintentionally detached, it is preferably secured by way of positive fit or friction fit with a blocking element.

In a further embodiment of the present invention, a securing element is formed by a preferably peripheral recess for accommodating a securing ring in the concave joint surface of the joint socket and/or joint insert.

In this embodiment, strain on the tissue during assembly can be avoided due to the use of a securing ring. This applies similarly to a snap connection secured through a securing ring.

An elongate strip made of a flexible material, which is more preferably preformed as a C-shaped ring, is preferably used as the securing ring. Said strip can be inserted lengthwise into the recess via an access opening or access recess extending from the rim of the concave joint surface to the peripheral recess.

In a further embodiment according to the invention, a securing element is formed by at least one recess in the joint socket and/or in the joint insert, which acts as a bayonet connection with a protrusion of a further securing element.

As already described above with regard to the thread, this securing means is also easy to assemble and detach. The advantage of this embodiment is that with a bayonet lock the securing elements are interlocked by application of both force and torque, and therefore the strain imposed on the tissue can be reduced as compared, for example, to using mere torque to assemble the joint.

In a further preferred embodiment of the invention, the joint socket and/or joint insert comprises an insertion aid which assists or enables the insertion of the respective convex joint surface into the associated concave joint surface.

Such an insertion aid can, of course, be used in the first and/or second partial joint, i.e. as an alternative, or as well as, between the joint insert and the convex surface of the joint head.

Said insertion aid offers the advantage, particularly where one partial joint is formed as an enarthrodial joint which, without an insertion aid, should be assembled prior to implantation only by pressing the joint parts together, that the press-in force is reduced or even avoided. At the same time, dislocation of the joint is prevented within the scope of the possible degree of movement of the implanted joint. Consequently, it is possible, due to an insertion aid, to intraoperatively assemble a partial joint which could otherwise be assembled only before implantation. As a result, the risk of dislocation due to strain endured during daily activities can be excluded.

The deformation necessary for assembling the partial joint is reduced or avoided in that the recess with its preferably elongate shape partially reduces the diameter of the convex joint surface. Owing to the insertion aid, the force, if any, required for insertion into the concave joint surface of the enarthrodial joint is so low that, particularly in the intraoperative setting, the strain on the patient tissue is reduced and damage to the joint components is prevented.

In a preferred embodiment of the invention, the insertion aid is formed as a preferably elongate recess in the convex joint surface of at least one of the partial joints.

The recess disposed on the sliding surface makes it easier to insert the convex joint surface into the concave joint surface of the respective partial joint. Depending on the dimensions of said recess, this insertion can be performed so that no deformation at all or only such deformation is produced that creates tension without damaging the materials of the joint socket or the insert. As a consequence, it is possible with this insert to achieve a higher degree of coverage of the enarthrodial joint than that which can be achieved when performing the insertion by using a snap connection for insertion. Moreover, the recess prevents any uncontrolled slipping out of position which may occur during assembly when performing the insertion by using, for instance, a snap connection.

The preferably elongate shape of the insertion aid on the convex joint surface particularly offers the advantage of allowing the insertion aid to be adjusted to the contour of the opening edge of the concave joint surface. Moreover, it is ensured in this way that, due to its minimal size, the insertion aid has the least possible impact on the geometry of the convex surface of the insert.

In a preferred embodiment of the present invention, the insertion aid is formed in a plane of symmetry of the convex joint surface.

In order to insert the convex joint component by means of the insertion aid, the two mating joint parts are tilted relative to each other. This means that the joint would have to be deflected to the same degree as during insertion in order for a dislocation to be caused. The arrangement of the insertion aid in a plane of symmetry of the convex joint surface has as a consequence that for there to be a dislocation, the partial joint would have to be deflected by almost 90°, irrespective of the orientation of the joint after implantation. Such a deflection is generally impossible both physiologically and on account of the prosthesis neck, especially as regards the hip joint.

An even better protection against dislocation can be achieved by taking into account the orientation of the insertion aid in the implanted state. In other words, the insertion aid is positioned on the convex joint surface of the partial joint so as not to be reached by physiological movement after the implantation. As regards, for instance, a hip joint, it is advantageous for the insertion aid to be placed behind the range of maximum adduction. In this regard, it may be advantageous not to have the insertion aid extend in a plane of symmetry or through the pole of the convex joint surface when taking into account a corresponding orientation of the joint in the implanted state.

Furthermore, the present invention provides an implantable joint component, in particular a joint insert for a double joint, and/or a joint head, with an insertion aid as described above.

Even though the insertion aid is advantageous in preventing dislocation mainly in double joints, the aforementioned advantages can also be achieved by the corresponding features when using a simple enarthrodial joint.

BRIEF DESCRIPTION OF THE FIGURES

Embodiment examples will now be described in detail with reference to the following Figures and description in order to provide a better understanding of the present invention. To this end, the features as are apparent from the Figures will be denoted by reference numbers. The same reference numbers will be used for different embodiment examples provided that the features in these embodiment examples are alike or achieve a similar effect.

DETAILED DESCRIPTION OF PREFERRED EMBODIMENTS

Figure 1:
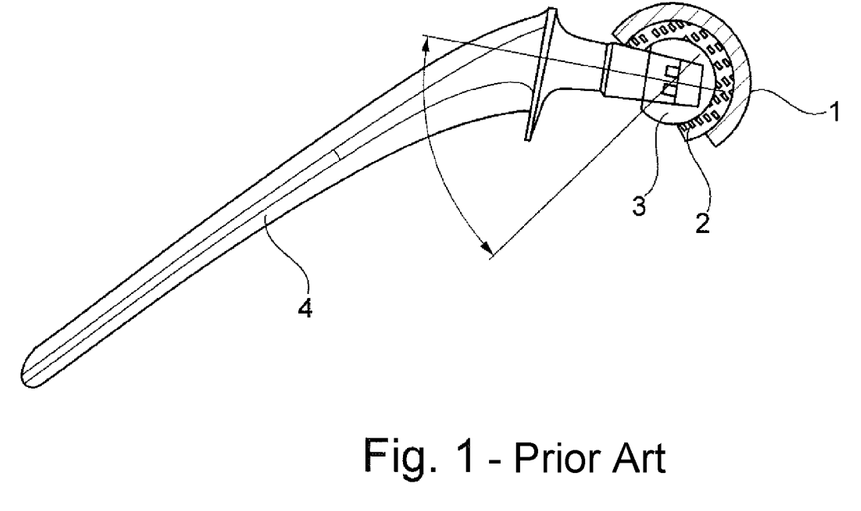
FIG. 1 shows an assembled joint replacement according to the invention, comprising two partial joints.

FIG. 1 shows the assembled state of a double-joint hip endoprosthesis which is also termed double mobility prosthesis. As already described above, prior art prostheses of this kind, despite having a small femoral head 3, provide the degree of movement of a large-head prosthesis. The implant, shown in the abduction position in FIG. 1, combines the advantages of less abrasion due to a smaller femoral head with the greater degree of movement provided by a large-head prosthesis as it is composed of two partial joints.

The first partial joint is situated between the hip socket 1 implanted in the pelvic bone and a joint insert 2. The second partial joint is formed between the joint insert 2 and the femoral head 3. As can be recognized in FIG. 1 from the deflection of the implant at a maximum abduction angle, the degree of movement is increased in that the prosthesis stem 4, situated below the femoral head 3, abuts against the rim of the joint insert 2 which, however, is deflected due to the movability of the first partial joint, as a result of which the degree of movement is increased until the prosthesis stem 4 abuts against the inner edge of the hip socket 3.

In the implant shown in FIG. 1, the first partial joint has, between the hip socket 1 and the joint insert 2, joint components of a ball joint which fall apart if no longer held together by external forces. By contrast, the second partial joint between the joint insert 2 and the femoral head 3 is an enarthrodial joint. In this joint, the joint insert 2 encloses the femoral head 3 beyond the equator thereof and is thus mounted thereon in such a way that the two joint components of the second partial joint will not fall apart even without the stabilizing impact of external forces.

Figure 2:
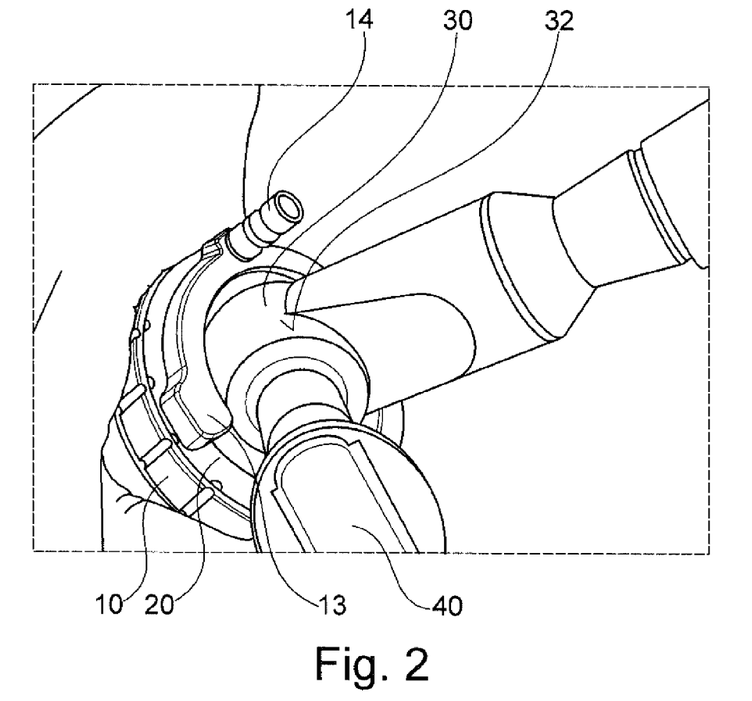
FIG. 2 shows a joint insert according to the invention, configured as an enarthrodial joint, during insertion of a joint head mounted on a prosthesis stem.

FIG. 2 shows a hip endoprosthesis according to the invention during insertion of the femoral head 30 into the joint insert 20. In this process, the joint head 30, which is connected to the prosthesis stem 40, is inserted into the concave joint surface 21 of the joint insert 20 by means of a pressing tool 50. A joint blocking means 13 ensures that, while the joint head 30 is being pressed in via the peripheral edge 23 of the concave surface 21 of the joint insert 20, the joint insert 20 cannot swivel relative to the joint socket 10 during use of the tool 50. For this purpose, the joint blocking means 13 is secured, as described further below, via a connecting element 14 to the rim 15 of the joint socket 10 which is situated between the exterior surface 17 of the joint socket 10 and the concave interior surface 11 of the joint socket or connects these. While being fastened in this manner, a portion of the joint blocking means extends above and beyond the rim of the joint insert 20 which is situated between the peripheral edge 23 of the concave joint surface 21 and the peripheral edge 24 of the convex joint surface 22. Advantageously, said portion of the joint blocking means 13 extends at an angle greater than 180° relative to the annular rim of the joint insert 20 in order to prevent dislocation of the joint insert in every direction.

It goes without saying that it is possible to provide such a joint blocking means 13 also for the joint head 30 in order to simplify the insertion of the joint head 30 into the concave joint surface 21 of the joint insert 20.

If the assembly of one or both partial joints is performed after implantation of the joint socket, the joint blocking means 13 may moreover be adapted to be used as an abutment by the pressing tool 50. With this type of configuration, the pressing tool is supported on the blocking means 13 so that ideally no force is applied to the surrounding bone tissue.

Furthermore, it can be recognized from FIG. 2 that, in its neutral position, i.e. when the rotational symmetry axes of the joint insert 20 and the joint socket 10 are superimposed on each other, the rim of the joint insert 20 is flush with the rim 15 of the joint socket 20. It is possible just as well to allow the peripheral edge of the joint insert 20 to protrude from the edge 15 of the joint socket 20 in the neutral position or starting position. As a result, the frequency of movement between the joint socket 10 and the joint insert 20 can be increased while maintaining the same degree of movement. In other words, deflection of the joint head 30 will cause the prosthesis stem 40 to contact the peripheral edge of the joint insert 20 earlier, and thus a forced relative movement between the insert 20 and the joint socket 10 will occur earlier as well. Since this may lead to increased abrasion, as is described above, the embodiment shown in FIG. 2 is preferred.

Figure 3A:
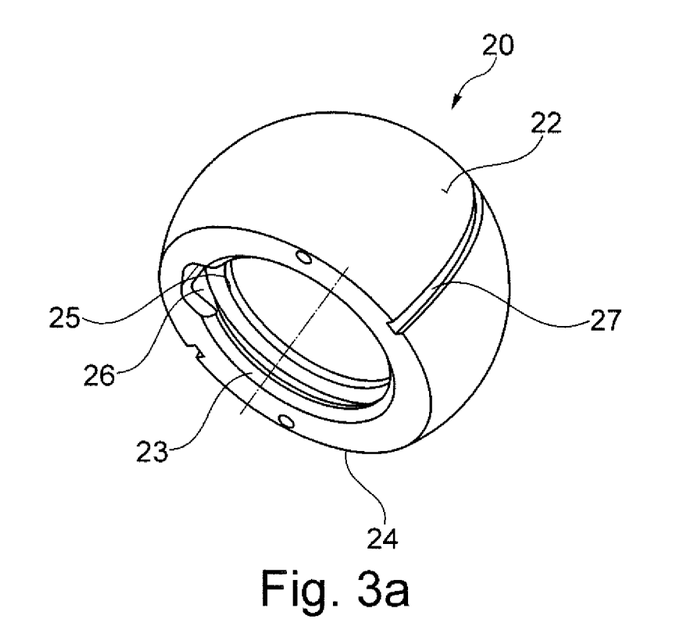
FIGS. 3a and 3b show an insert according to the invention which has an insertion aid on its convex joint surface.
Figure 3B:
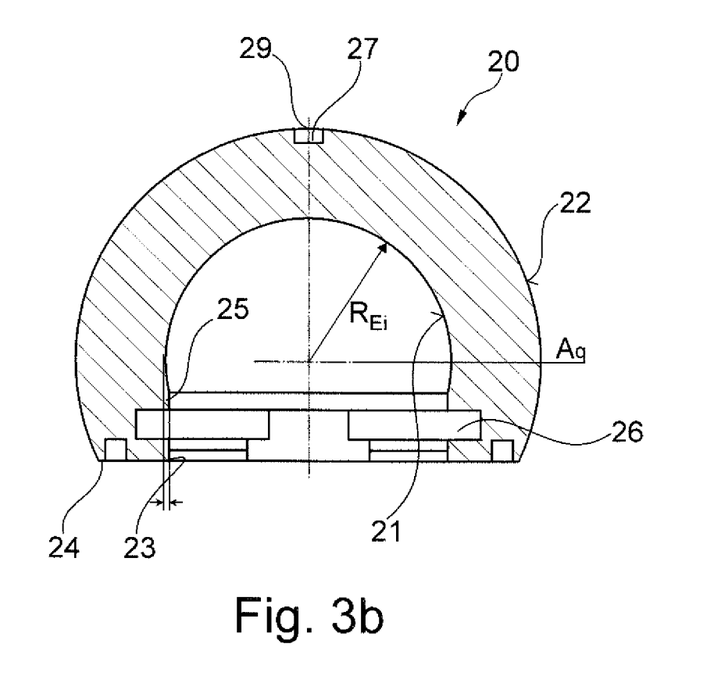

FIGS. 3a and 3b show a joint insert 20 according to the invention. As can be recognized from FIG. 3b, the concave joint surface 21 of the joint insert 20 is formed as an enarthrodial joint. The same applies to the concave joint surface 11 in the sectional view of the joint socket 10 shown in FIG. 4b. Consequently, the concave receptacle in both partial joints has an insertion opening smaller than the convex joint surface to be received therein, and therefore the assembly of the partial joints requires the use of force and/or an insertion aid 27.

Figure 4A:
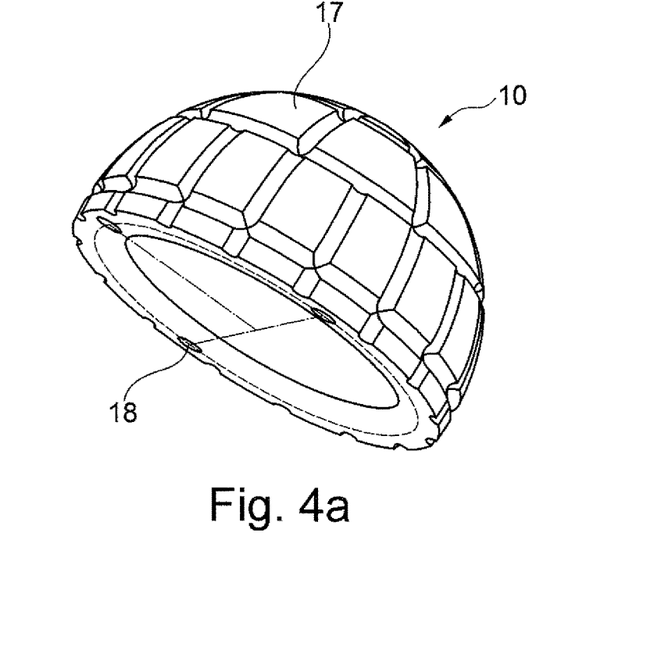
FIGS. 4a and 4b show an implantable joint socket according to the invention.
Figure 4B:
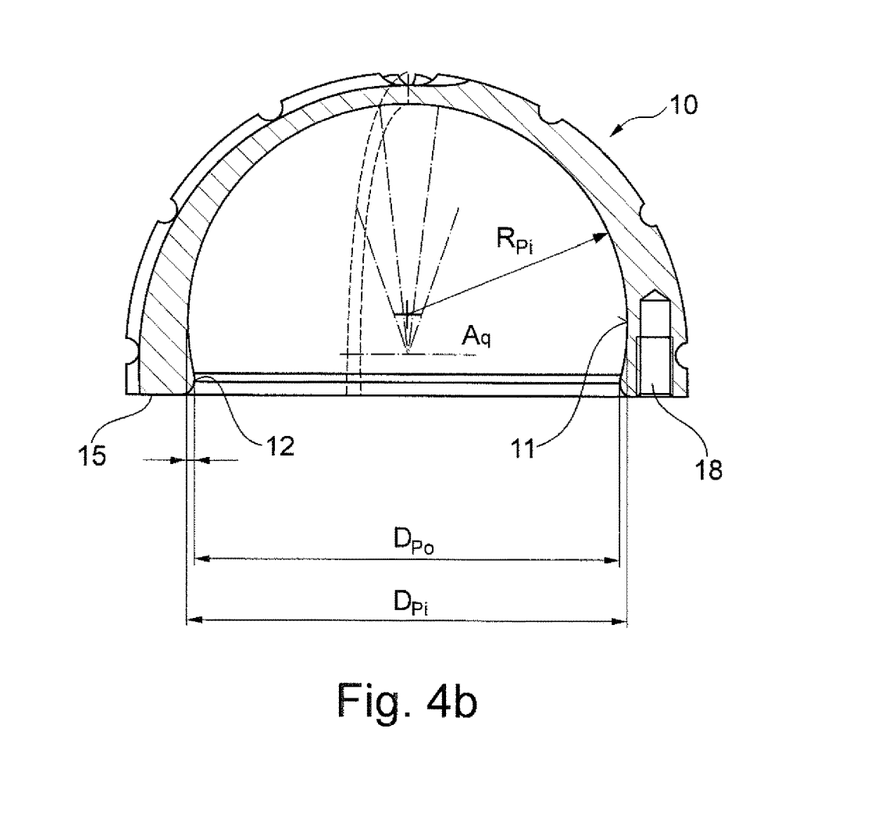

Since, in the embodiment example shown in FIGS. 3 and 4, both partial joints have a spherical shape, the radius $R_{Ei}$ of the concave joint surface 21 is larger than the radius of the opening of the receptacle formed by the concave joint surface 21, and the diameter $D_{Pi}$ of the concave joint surface 11 of the joint socket 10 is greater than the diameter $D_{Po}$ of the joint socket opening.

Not only is the joint insert 20 in FIGS. 3a and 3b configured as an enarthrodial joint in the region of the concave joint surface 21, but it moreover has an additional securing means in the region 25 extending beyond the equator which is in the form of a recess 26 directed towards the opening of the concave joint surface 21. This means is provided for insertion of a securing ring. In the shown embodiment example, the joint insert 20 is thus designed to have two securing means on the side of the second partial joint, which prevent separation of the convex joint surface 32 of the joint head 30 from the concave joint surface 21 of the joint insert 20. However, it is possible just as well to provide just one of the securing means 25, 26 in order to prevent dislocation of the respective partial joint.

An elongate strip made of a flexible material is preferably used as the securing ring. Preferably, the elongate strip is preformed in a C-shape. In order to introduce the securing ring into the peripheral recess 26, it is pushed lengthwise into the recess 26 through an access opening or access recess extending from the rim of a concave joint surface 11, 21 to the recess 26. Where the flexible C-shaped securing ring is not preformed, it will take on the C-shape only upon introduction into the peripheral recess 26. As an alternative, it is also possible to use a circlip as the securing ring.

Furthermore, the joint insert 20 as shown in FIGS. 3a and 3b has an insertion aid 27 in the form of an elongate groove on the side of the first partial joint, i.e. on the convex surface 22 of the joint insert 20. This groove 27 extends from the peripheral edge 24 of the convex joint surface 22 via the pole 29 and back to the peripheral edge 24. The points of contact of the groove 27 with the peripheral edge 24 are diametrically opposed to each other in the shown embodiment example since the insertion aid 27 is situated in a plane of symmetry of the spherical convex joint surface 22.

The joint socket 10 as shown in FIGS. 4a and 4b, which forms the receptacle for the first partial joint, has a spherical-segment-shaped concave joint surface 11 as well as an exterior surface 17 provided for implantation into the bone tissue of a patient. The exterior surface 17 may be anchored in the bone tissue by means of different techniques known from the prior art. As already described above, the joint socket 10 as well as the joint insert 20 have a region 12 which, as a securing means, prevents dislocation of the first partial joint, i.e. prevents the joint insert 20 from popping out.

Furthermore, fastening means 18 are provided in the peripheral region formed between the exterior surface 17 and the concave joint surface 11 of the joint socket 10. In the present embodiment example, the fastening means 18 are a threaded hole and two stop holes, by means of which the joint blocking means 13 of FIG. 2 is detachably fastened via a connecting element 14. As can be seen from FIGS. 2 and 4, the threaded hole 18 of the joint socket 10 is situated on the circumference of the peripheral region, offset in each case by 90°, between said two diametrically opposed stop holes.

It will now be explained with reference to FIGS. 5a and 5b how an insertion aid 27 assists the insertion of a joint insert 20 into a joint socket 10. However, anything stated below and above also applies directly to the partial joint formed by the concave joint surface 21 of the joint insert 20 and the convex joint surface 32 of the joint head 30.

Figure 5A:
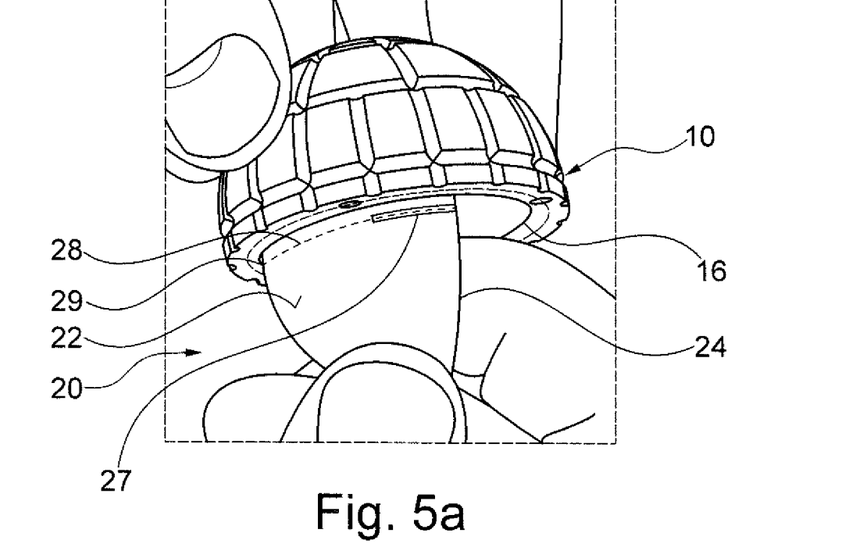
FIGS. 5a and 5b show the insertion of a joint insert according to the invention by means of an insertion aid configured in an elongate shape.
Figure 5B:
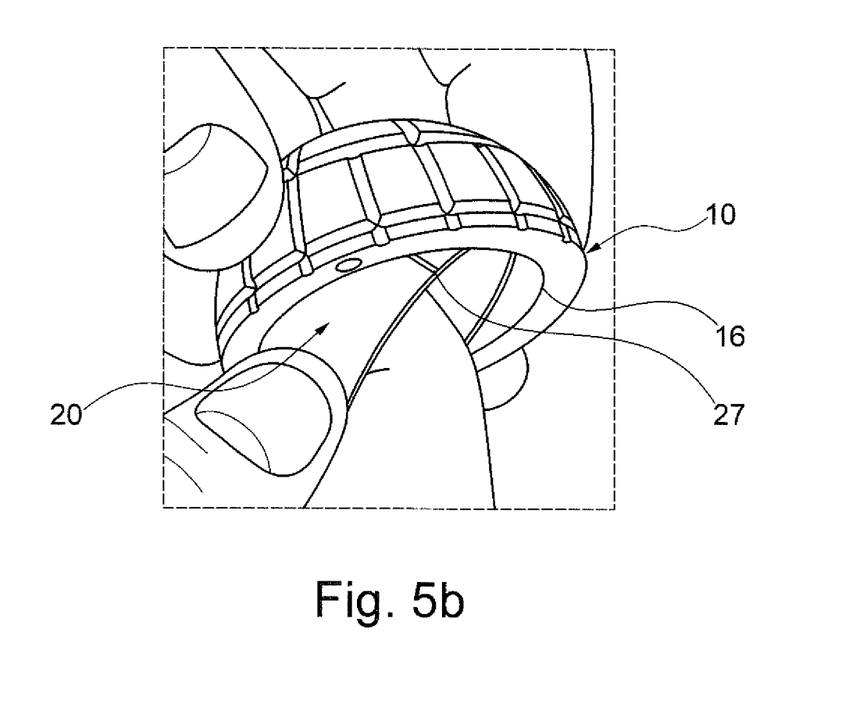

FIGS. 5a and 5b show a joint insert 20 according to the invention during insertion into a joint socket 10. In the present embodiment example, the joint socket 10 and the joint insert 20 are components of a double mobility hip joint endoprosthesis. The joint socket 10 has an inner concave joint surface 11 that cooperates with the convex joint surface 22 of the joint insert 20. The opening of the concave joint surface 11 of the joint socket 10 is delimited by a peripheral edge 16, and its diameter is smaller than the diameter of the concave joint surface 11 at the height of the equator of the joint socket 10.

As can furthermore be recognized from FIGS. 5a and 5b, the convex joint surface 22 of the insert 20 has an insertion aid 27 situated in a plane of symmetry of the insert 20 or the convex joint surface 22. The shown insertion aid 27 is configured as an elongate recess extending from the peripheral edge 24 towards the pole 29 of the convex joint surface 22. The elongate recess 27 is situated in the plane of symmetry of the convex joint surface 22, indicated by the auxiliary line 28.

Given that the insertion aid 27 extends as far as up to the peripheral edge 24 of the convex surface 22, it is possible to facilitate the transportation of synovial fluid between the convex surface 22 of the insert 27 and the concave surface 11 of the socket 10 as well as the removal of possible abrasion products between these surfaces, and thus to increase the service life of the joint endoprosthesis.

The elongate recess starts at the peripheral edge 24 of the convex surface 22 and extends, in FIGS. 5a and 5b, over approximately one third of the length of the auxiliary line between the pole 29 and the edge 24. Preferably, the elongate recess extends over 25% to 75% of the length of the connecting line. However, as can be recognized from FIGS. 3a and 3b, the recess 27 may also extend over the entire convex joint surface of one joint part.

It will be understood that the elongate recess does not necessarily have to be in contact with the peripheral edge 24 of the convex surface 22, but may also be arranged with both ends in the convex surface 22 of the joint insert 20. Furthermore, the insertion aid 27 may be configured to include multiple components. For instance, it is possible to provide a further component of the insertion aid 27 on the opposite side of the joint surface 22, symmetrically to the insertion aid 27 shown in FIG. 5a.

The longer and broader the insertion aid 27, the easier it is for the joint insert 20 to be inserted into a joint socket 10 configured as an enarthrodial joint. It should be noted, however, that as the length and/or width increases, the convex surface of the insert becomes more irregular, which may entail a local increase in tension.

The shape of the recess is preferably configured to match the contour of the edge of the associated concave joint surface that serves as the mating joint part of the partial joint. When placed against the joint socket 10, the recess of the insertion aid 27 with its bottommost section comes into contact, preferably at least via a section of its recess base, with the peripheral edge 16 of the concave receptacle of a mating joint part, here the joint socket 10. Most preferably, the recess 27 has in its longitudinal direction a contour with a radius that is substantially the same as the radius $R_{Pi}$ of the joint socket 10 at its peripheral edge 16. Preferably, the insertion aid 27 gradually merges, at least at one of its ends in the longitudinal direction, into the convex surface of the insert.

The cross-section of the elongate recess is configured to prevent peak stresses being generated in the region of the transition from the insertion aid 27 to the joint surface 22. For this reason, it is preferred for the insertion aid to seamlessly merge into the convex joint surface 22 of the joint insert 20.

In the shown embodiment, the recess-shaped insertion aid 27 is disposed on the auxiliary line 28 between the edge of the convex joint surface 22 and its pole 29. In other words, the plane formed by the recess makes an angle of 0° with the plane defined by the auxiliary line 28. Even though this is the preferred embodiment, it is easily possible to select any other angle.

In other words, the angle between the insertion aid 27 and the auxiliary line 28 may range from 0° to 90°, preferably, however, from 0° to 45°, and even more preferably from 0° to 15°. The principle generally applies that the smaller the angle between the insertion aid 27 and the imaginary auxiliary line 28, the lower the probability that the insertion aid 27 will become flush with the opening edge of the joint socket during movement of the joint, which may give rise to dislocation.

As an alternative, it is possible to offset the plane defined by the insertion aid 27 in parallel to the plane defined the auxiliary line 28 and/or the plane of symmetry of the convex joint surface 22.

Such free positioning of the insertion aid 27 on the convex surface 22 of the insert 20 permits optimization in terms of ease of mounting of the joint insert 20 in a joint socket 10 or of a joint head 30 in a joint insert 20. This makes it possible to take into account the strain still imposed, despite the insertion aid 27, on the implant material during assembly of the artificial joint. It is also possible to reduce the strain imposed on the material of the joint socket 10, the insert 20 and/or the joint head 30 depending on the implantation site and the strain resulting therefrom. Thus, the insertion aid 27 makes it possible to produce the joint socket 10 and particularly the joint insert and/or the joint head 30 from a relatively inelastic material such as, for example, metal or ceramics.

Since in the shown embodiment, the insertion aid 27 is arranged on the auxiliary line 28, i.e. in a plane of symmetry of the joint insert 20, and thus at an angle of 0°, insertion of the joint insert 20 into the joint socket 10 is performed by tilting the two components relative to one another by about 90° prior to insertion. If the insertion aid 27 is arranged at a different angle, the joint socket 10 and the joint insert 20 must correspondingly be oriented differently with respect to one another so as to allow assembly.

After orientation, the insertion aid 27 is placed on the peripheral edge 26 of the concave joint socket surface 11 such that the peripheral edge 16 is disposed within the recess of the insertion aid 27. In this way, the insert 20 is situated, in the plane of the opening of the concave joint surface 11, at a position slightly offset relative to the mounted state, and thus fits through the opening formed by the concave joint surface 11. To put it differently, the offset compensates for the oversize of the joint insert 20 in proportion to the opening of the joint socket 10.

In other words, the joint insert 20 fits into the concave joint surface 11 of the joint socket 10 since, owing to the depth of the insert aid 27, the diameter of the joint insert 20 is smaller than or equal to the diameter of the peripheral edge 16 of the concave joint surface 11 at the height of the peripheral edge 24 of the convex surface 22 of the joint insert 20.

In FIG. 5b, the joint insert 20 is shown in a slightly inclined position after its successful insertion into the joint socket 10. Furthermore, it can be recognized that the joint insert 20 of this embodiment example has a concave joint surface 21 provided for receiving a joint head 30 (see FIG. 2).

In any case, the present invention provides a joint endoprosthesis which, while being dislocation-free, is easy to assemble during surgery.

REFERENCE NUMERALS

1 Joint socket (prior art)
2 joint insert (prior art)
3 joint head (prior art)
4 joint stem (prior art)
10 joint socket
11 concave joint surface of the joint socket
12 means for securing the joint socket: protrusion
13 joint blocking means 14 connecting element
15 peripheral rim of the joint socket
16 peripheral edge of the joint socket
17 exterior surface of the joint socket
18 fastening means
20 joint insert
21 concave joint surface of the joint insert
22 convex joint surface of the joint insert
23 peripheral edge of the concave joint surface of the joint insert
24 peripheral edge of the convex joint surface of the joint insert
25 means for securing the joint insert: protrusion
26 means for securing the joint insert: recess for securing ring
27 insertion aid: recess
28 auxiliary line on the convex joint surface of the joint insert 20 which extends in the plane of symmetry thereof
29 pole of the convex joint surface 22
30 joint head
32 convex joint surface of the joint head
40 prosthesis stem
50 pressing tool
Aq equator of a convex or concave joint surface
$R_{P1}$ inner radius of the joint socket
$D_{P1}$ inner joint diameter of the joint socket
$D_{P0}$ joint opening diameter of the joint socket
$R_{E1}$ inner radius of the joint insert
$D_{E0}$ inner joint diameter of the joint insert
$D_{Ei}$ joint opening diameter of the joint insert

The invention claimed is:

1. A joint replacement with
a joint socket (10) having a concave surface (11), and
a joint insert (20) having a concave (21) and a convex (22) joint surface,
which are each delimited by a peripheral edge (23, 24),
the convex joint surface (22) of the joint insert (20) being designed, in the assembled state, to form at first partial joint with the concave joint surface (11) of the joint socket (10),
the concave joint surface (21) of the joint insert (20) being designed, in the assembled state, to form a second partial joint with the convex joint surface (32) of a joint head (30), and the joint socket (10) and the joint insert (20) each having a securing means (12, 25, 26) for preventing dislocation of the joint replacement,
wherein the joint head (30) and/or the joint insert (20) comprises an insertion aid (27, 28), with which the insertion of the respective convex joint surface (22, 32) into the corresponding concave joint surface is enabled,
the insertion aid (27) is formed as an elongate recess in the convex joint surface (22, 32) of at least one of the partial joints,
the joint replacement is an enarthrodial joint,
wherein each partial joint comprising the insertion aid forms a ball and socket joint with the concave joint surface enclosing the convex joint surface beyond the equator thereof, wherein the enarthrodial joint is capable of motion around multiple axes, which have one common center,
wherein a region (12, 25) of the concave joint surface (11, 21) of the joint socket (10) and/or of the joint insert (20) prevents dislocation of the respective partial joint by forming the respective joint into an enarthrodial joint,
wherein the securing means (12, 25, 26) of at least one of the partial joints is of a type which has two detachable securing elements which cooperate by means of a detachable threaded, locking or snap connection to prevent dislocation of the partial joint, and
wherein at least one of the two securing elements is formed by a peripheral recess (26) to accommodate a securing ring in the concave joint surface (11, 21) of the joint insert (20).

2. The joint replacement according to claim 1, wherein at least one of the two securing elements is formed by a peripheral recess (26) to accommodate a securing ring in the concave joint surface (11, 21) of the joint insert (20).

3. The joint replacement according to claim 1, wherein the insertion aid (27) is formed in a plane of symmetry of the convex joint surface (22, 32) of the joint insert.

4. The joint replacement according to claim 1, wherein the insertion aid (27) is formed in a plane of symmetry of the convex joint surface (22, 32) of the joint insert.

5. The joint replacement according to claim 1, wherein the opening diameter ($D_{Po}$) of the concave joint surface (11) of the joint socket is 1% to 6% less than a joint diameter ($D_{Pi}$), and the opening diameter ($D_{Eo}$) of the concave joint surface (21) of the joint insert is 1% to 6%-less than a joint diameter ($D_{Ei}$).

* * * * *